United States Patent [19]
Li

[11] Patent Number: 6,139,585
[45] Date of Patent: *Oct. 31, 2000

[54] BIOACTIVE CERAMIC COATING AND METHOD

[75] Inventor: Panjian Li, Mansfield, Mass.

[73] Assignee: Depuy Orthopaedics, Inc., Warsaw, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/038,444

[22] Filed: Mar. 11, 1998

[51] Int. Cl.$^7$ .................................... A61F 2/28
[52] U.S. Cl. ................. 623/23.57; 427/2.24; 623/23.56; 623/23.6
[58] Field of Search ................. 623/16, 11, 18, 623/11.11, 16.11, 18.11; 427/2.24

[56] References Cited

U.S. PATENT DOCUMENTS

| | | | |
|---|---|---|---|
| 4,285,223 | 8/1981 | Das et al. | 72/42 |
| 5,178,845 | 1/1993 | Constantz et al. | 423/305 |
| 5,188,670 | 2/1993 | Constantz | 118/667 |
| 5,205,921 | 4/1993 | Shirkanzadeh | 205/318 |
| 5,231,169 | 7/1993 | Constantz et al. | 530/356 |
| 5,279,831 | 1/1994 | Constantz et al. | 424/423 |
| 5,336,264 | 8/1994 | Constanz et al. | 623/16 |
| 5,397,362 | 3/1995 | Noda | 623/16 |
| 5,441,536 | 8/1995 | Aoki et al. | 427/2.27 |
| 5,455,231 | 10/1995 | Constantz et al. | 514/21 |
| 5,496,399 | 3/1996 | Ison et al. | 106/35 |
| 5,545,226 | 8/1996 | Wingo et al. | 623/16 |
| 5,569,442 | 10/1996 | Fulmer et al. | 423/311 |
| 5,571,493 | 11/1996 | Fulmer et al. | 423/308 |
| 5,580,623 | 12/1996 | Fulmer et al. | 428/34.1 |
| 5,612,049 | 3/1997 | Li et al. | 424/422 |
| 5,683,461 | 11/1997 | Lee et al. | 623/16 |
| 5,683,496 | 11/1997 | Ison et al. | 106/35 |
| 5,683,667 | 11/1997 | Fulmer et al. | 423/311 |
| 5,697,981 | 12/1997 | Ison et al. | 623/16 |
| 5,728,395 | 3/1998 | Ohtsuka et al. | 424/422 |
| 5,759,376 | 6/1998 | Teller et al. | 205/50 |
| 5,817,326 | 10/1998 | Nastasi et al. | 424/426 |
| 5,820,632 | 10/1998 | Constantz et al. | 424/423 |
| 5,824,087 | 10/1998 | Aspden et al. | 623/16 |
| 5,868,796 | 2/1999 | Buechel et al. | 623/16 |
| 5,900,254 | 5/1999 | Constantz | 424/423 |
| 5,958,430 | 9/1999 | Campbell et al. | 424/400 |
| 5,958,504 | 9/1999 | Lee et al. | 427/2.24 |

FOREIGN PATENT DOCUMENTS

| | | | |
|---|---|---|---|
| 0389713 | 3/1990 | European Pat. Off. | A61L 27/00 |
| 0 437 975 A1 | 12/1990 | European Pat. Off. | A61L 27/00 |
| 840711 | 2/1996 | Japan | A61L 27/00 |
| WO 97/41273 | 11/1997 | WIPO | C23C 4/18 |
| WO 98/28025 | 7/1998 | WIPO | A61L 27/00 |

*Primary Examiner*—David H. Willse
*Assistant Examiner*—Suzette J. Jackson
*Attorney, Agent, or Firm*—Nuttter, McClennen & Fish, LLP

[57] ABSTRACT

A bioactive bone mineral carbonated nano-crystalline apatite is chemically bonded to a variety of substrates, including implantable prostheses. This coating is applied uniformly to substrate surfaces of varying geometry and surface textures. It is firmly secured to the substrate and encourages rapid and effective bone ingrowth. The coating is applied by immersing the substrate in an aqueous solution containing calcium, phosphate and carbonate ions. Other ions, such as sodium, potassium, magnesium, chloride, sulfate, and silicate, may optionally be present in the solution. The solution is exposed in a controlled environment when it reacts with the substrate to form the coating.

9 Claims, 4 Drawing Sheets

BIOACTIVE CERAMIC COATING AND METHOD

CROSS-REFERENCE TO RELATED APPLICATIONS

Not applicable

STATEMENT REGARDING FEDERALLY SPONSORED RESEARCH

Not applicable

BACKGROUND OF THE INVENTION

The invention relates to bioimplantable articles having a bioactive ceramic coating, which reassembles bone mineral, and to methods for forming such coating on implantable articles.

It is desirable to apply mineralized and/or ceramic coatings to a variety of articles. Biological implants including joint prostheses and dental implants represent one class of articles to which such coatings are frequently applied. The substrate to which these coatings is applied is usually a metal or a plastic, but the coatings can be applied to other substrates such as ceramic and silicon.

Biological implants, such as joint and dental prostheses, usually must be permanently affixed or anchored within bone. In some instances it is acceptable to use a bone cement to affix the prosthesis within bone. In the case of many joint prostheses, however, it is now more common to affix the joint prosthesis by encouraging natural bone ingrowth in and around the prosthesis. Bone-to-implant interfaces that result from natural bone ingrowth tend to be stronger over time and more permanent than are bone cement-prosthesis bonds.

Optimal bone ingrowth requires that natural bone grow into and around the prosthesis to be implanted. Bone ingrowth and prosthesis fixation can be enhanced by providing irregular beaded or porous surfaces on the implant. Although various materials, including titanium alloys, are biocompatible, they are not necessarily bioactive because they can neither conduct bone formation nor form chemical bonds with bone.

Thus, enhanced fixation of implants within bone can be attained by coating the implant with a bioactive mineralized and/or ceramic material. Such coatings have been shown to encourage more rapid bone ingrowth in and around the prosthesis.

Various techniques are used to apply mineralized and/or ceramic coatings to bioimplantable substrates. These coatings are typically made of ceramics and tend to be characterized by a relatively large crystal size. These coatings can be applied by a variety of techniques including plasma spraying, ion implantation, and sol-gel processing. These coating methods, although relatively widely used, do have some drawbacks. For example, the applied coatings tend to possess micropores and macropores and they can be relatively thick and brittle. These coatings can also possess chemical defects, and they do not always adhere well to substrates. Finally, such coatings are not evenly and uniformly applied to surfaces with complex geometries, such as porous surfaces with undercut regions.

It has been well documented that calcium phosphate ceramics, especially hydroxyapatite, can conduct bone formation. Hydroxyapatite ceramic has been successfully applied as a coating on cementless metallic implants to achieve quick and strong fixation. Thermal plasma spraying is one of the more common methods used to produce hydroxyapatite coatings. However, the resulting plasma-sprayed hydroxyapatite coating is of relatively low density and is not uniform in structure or composition. The adhesion between the coating and substrate is generally not very strong, especially after long term exposure within the body. The generation of hard ceramic particles, resulting from the degradation of thermal plasma sprayed coating, and coating delamination, are major concerns.

Low temperature processes have also been implemented to produce hydroxyapatite ceramic coatings using water-based solutions. Since aqueous solutions can reach any open space, these low-temperature processes can be efficiently used in the case of substrates with complex surface geometries. The hydroxyapatite coating that is formed from this solution can be more biologically friendly to bone tissue than is the plasma-sprayed hydroxyapatite coating which is produced by a high temperature process. However, currently known low temperature processes typically require pretreatment of the substrate.

One example of an aqueous system-based coating technique is disclosed in U.S. Pat. No. 5,205,921 in which bioactive ceramic coatings are electrodeposited upon a substrate. Bunker et al., *Science* 264, 48–55 (1994) disclose a technique for applying an octacalcium phosphate upon a substrate by immersing the substrate in a solution containing calcium chloride after surface treating the substrate with a material such as chlorosilane. Other techniques, such as disclosed in Japanese Patent Application No. 8-40711, form a hydroxyapatite coating by exposing the substrate to calcium phosphate in a pressure reactor. U.S. Pat. No. 5,188,670 discloses a technique for forming a hydroxyapatite coating on a substrate by directing a stream of liquid containing hydroxyapatite particles to apply a fibrous, crystalline coating of hydroxyapatite.

Despite the existence of ceramic coatings and various processes for producing such coatings, there remains a need for improved and reliable processes used to apply bioactive ceramic coatings to substrates.

SUMMARY OF THE INVENTION

The invention provides a dense, substantially pure ceramic coating with a crystal size of less than 1 micrometer. The coating forms a good chemical bond to substrates to which it is applied. Preferably, the coating is a bioactive ceramic coating in the form of a bone mineral carbonated nano-crystalline apatite with chemically adsorbed water having a crystal size of less than about 1 micrometer. The coating contains calcium, magnesium, carbonate and phosphate. Optionally, the coating also includes ions or ionic groups selected from the group consisting of sodium, chlorine, sulfates, silicate and mixtures thereof. Preferably, the ratio of carbonate groups to phosphate groups in the coating is in the range of about 1:100 to 1:3. Further, the atomic ratio of magnesium to calcium is in the range of about 1:100 to 1:4.

The coating can be applied to a variety of substrates, including silicon, metals, ceramics, and polymers. It is particularly useful for application to bioimplantable substrates such as bone and dental prostheses. The coating can be uniformly applied to substrate surfaces that have complex geometries and surface features, including porous beaded substrates. The thickness range of the coating can vary from about 0.005 to 50 micrometers.

The coating can be effectively and efficiently applied to a variety of substrates. According to the method of the invention, there is first provided an aqueous solution comprising calcium, magnesium, phosphate, and carbonate ions with a pH in the range of about 5–10 and temperature less than about 100° C. Optionally, the solution also includes ions of sodium, potassium, chlorine, sulfate, silicate and mixtures thereof. A suitable substrate is then at least partially immersed in the solution for an amount of time sufficient for the solution to react with the substrate to form a bone mineral ceramic coating and effect the chemical bonding of the coating to the substrate. During the process the solution can be exposed in a controlled environment to an artificial atmosphere having about 0.001 to 10 mole percent carbon dioxide and a balance of gas or gases selected from the group consisting of oxygen, nitrogen, argon, hydrogen, water steam, ammonia, and mixtures thereof. One particular advantage of the process of the invention is that the coating can be applied at ambient pressures.

DETAILED DESCRIPTION OF THE INVENTION

The invention provides a substantially pure ceramic coating that is chemically bonded to a substrate. The coating is a bioactive, amorphous calcium phosphate that is apatitic and which contains carbonate groups and, optionally, magnesium ions. As used herein, an amorphous calcium phosphate refers to and includes a ceramic that is nano-crystalline, having a crystal size of less than about 1 micrometer.

The coating is particularly useful with bioimplantable substrates such as bone prostheses and dental implants in that the coating can be firmly adhered to the surface of the substrate in a uniform manner, regardless of the surface geometry or surface texture of the substrate. Further, the coating is a bone mineral-like in nature, chemically resembling natural bone, so it is able to promote effective and rapid growth of natural bone in and around the substrate so as to firmly affix the substrate in place.

The coating is preferably a bone mineral carbonated nano-crystalline apatite with chemical adsorbed water and having a crystal size less than about 1 micrometer. Ions present in the coating include calcium, magnesium, carbonate, and phosphate. Further, the coating optionally includes sodium, potassium, chlorine, sulfates, silicate and mixtures thereof. The molar ratio of carbonate groups to phosphate groups is generally in the range of about 1:100 to 1:3. The atomic ratio of magnesium to calcium present in the coating is in the range of about 1:100 to 1:4.

The coating is characterized by an absence of macropores and micropores, and it is similar in composition to bone. The crystal size is less than about 1 micrometer and is so small that ceramic crystals cannot be detected by thin-film x-ray diffraction techniques. The small crystal size, and the presence of carbonate groups and magnesium ions contribute to the bone mineral-like nature of the coating. The bone mineral-like properties of the coating also facilitate rapid and effective bone ingrowth.

The coating of the invention is also considered to be dense. The term "dense" as used herein refers to a coating that is substantially free of both micropores and macropores.

Figure 1:
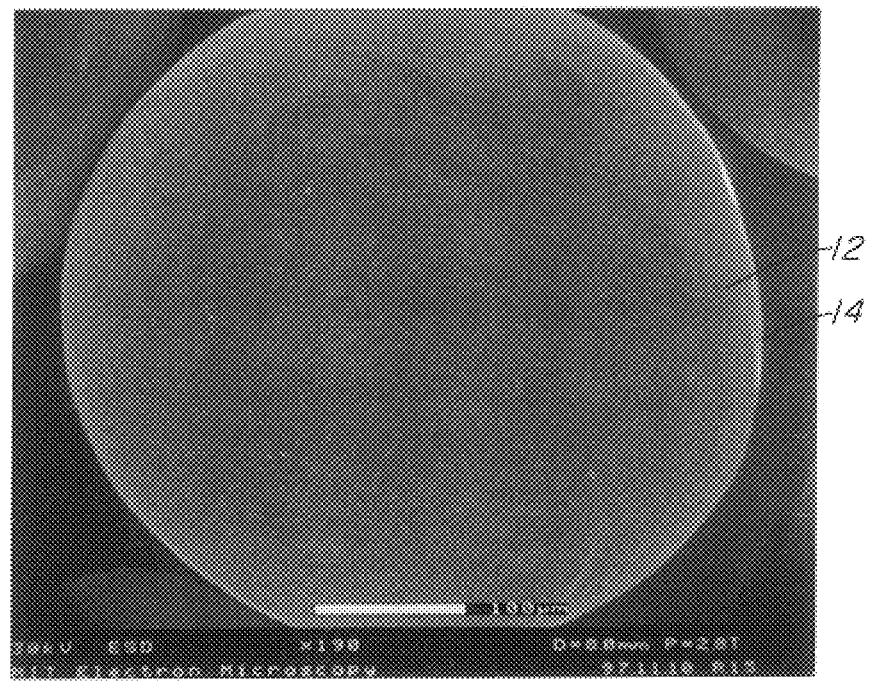
FIG. 1 is a photomicrograph at 190 × magnification, showing a coating according to the present invention applied to a Ti6A14V joint prosthesis component bead including Ti6A14V beads.
Figure 2:
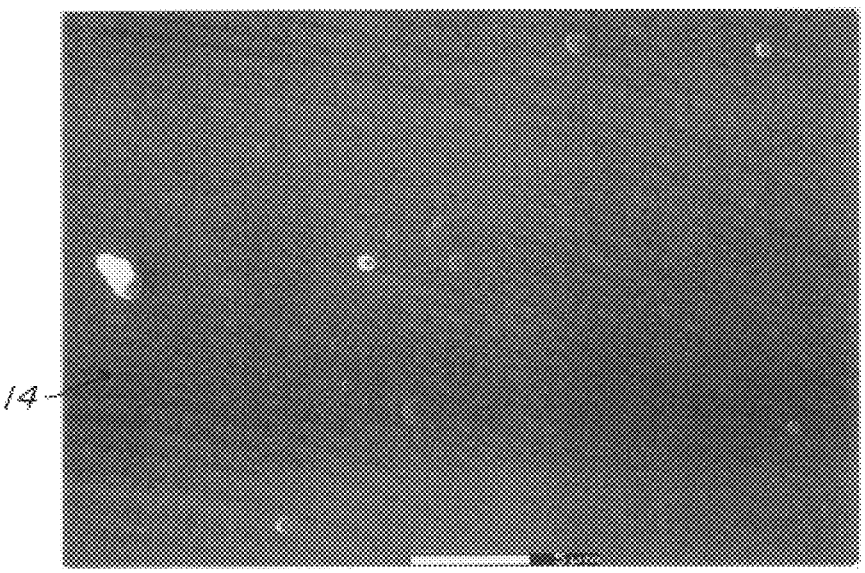
FIG. 2 is a photomicrograph of the coating shown in FIG. 1 at 3000 × magnification.
Figure 3:
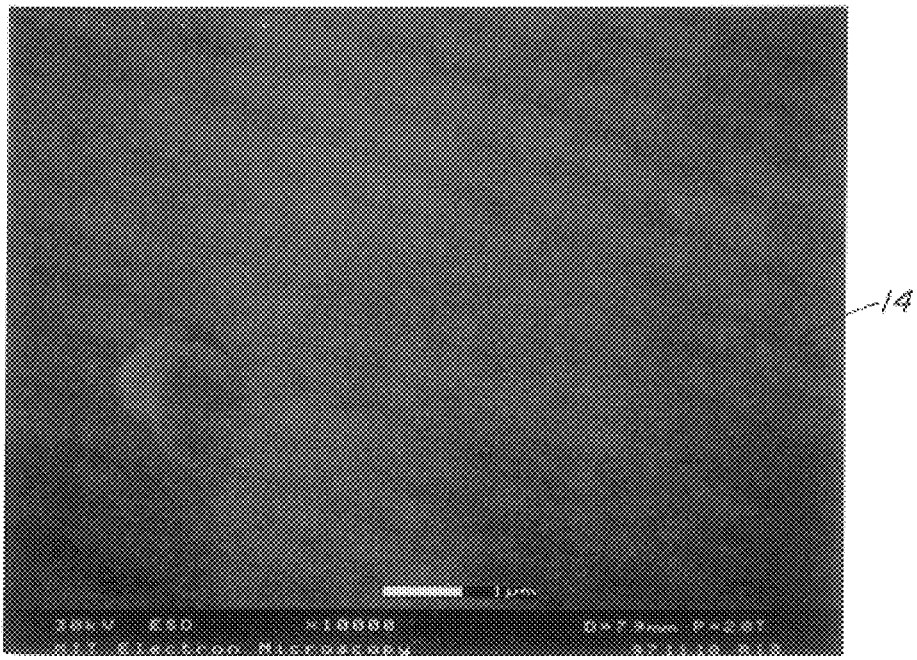
FIG. 3 is a photomicrograph of the coating shown in FIG. 1 at 10000 × magnification.

FIGS. 1–3 illustrate the coating quality and uniformity obtained according to the present invention. The coating shown is that obtained according to Example VIII in Tables 4 and 5. FIG. 1 illustrates a Ti6A14V substrate 10, in the form of a component of a joint prosthesis, having Ti6A14V beads 12 affixed thereto to provide a porous surface texture. The substrate and beads are coated with a bone mineral-like ceramic 14 according to the present invention. FIGS. 1–3 illustrate the smooth and uniform nature of the coating. The amorphous and/or nano-crystalline nature of the coating is also apparent from the photomicrographs of FIG. 1–3.

Figure 4:
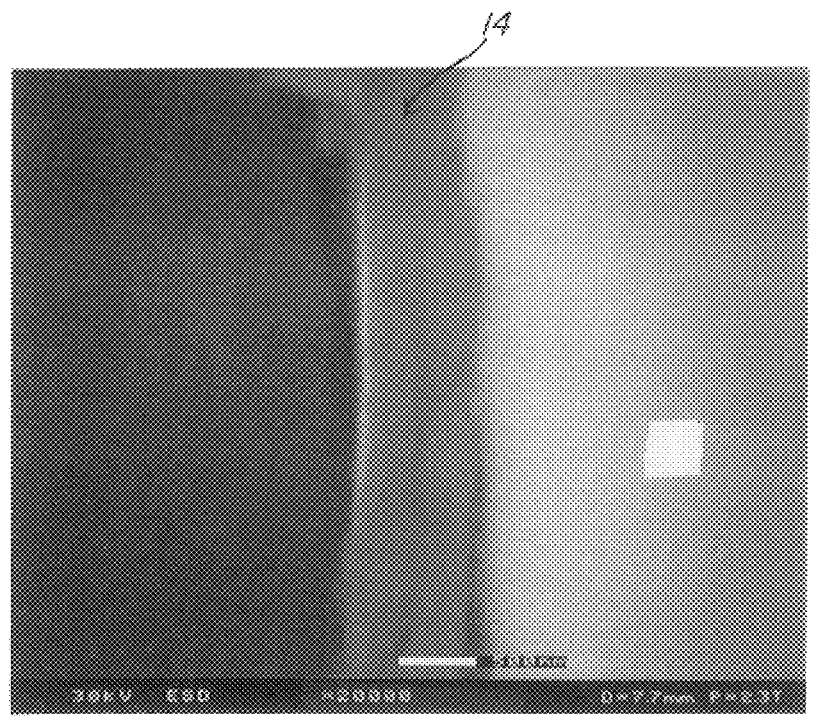
FIG. 4 is a cross-section of a substrate bearing the coating of the present invention.

FIG. 4 is a cross sectional view of a substrate 10 bearing the bone mineral-like coating 14 of the invention. In the illustrated embodiment, the coating is present at a thickness of about 0.7 micrometers.

Figure 5:
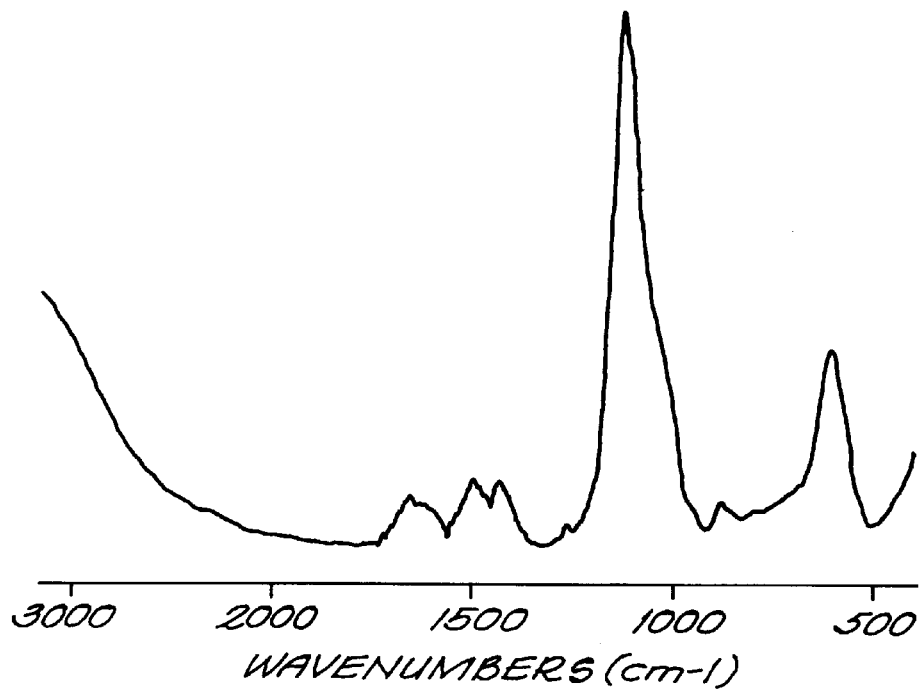
FIG. 5 is a Fourier Transform Infrared (FT-IR) reflectance spectrum obtained for the coating shown in FIG. 4.

FIG. 5 is a FT-IR spectrum of the coating shown in FIG. 4. This confirms that the calcium phosphate within the coating is a poorly crystallized apatite. The peaks ranging from 1350–1700 cm$^{-1}$ are attributed to carbonate groups, indicating incorporation of carbonate groups into the apatite.

Chemical analysis of the ceramic coating shown in FIG. 5, upon dissolution in 0.002N HCl, established the similarity of the coating to bone mineral. The molar rations of selected functional groups present in this coating is shown in Table 1, below.

TABLE 1

| Groups | Molar Ratios Ratio |
|---|---|
| $Ca^{2+}/PO^{3-}_4$ | 1.60 |
| $Ca^{2+}/Mg^{2+}$ | 6.31 |
| $(Ca^{2+}/Mg^{2+})/PO^{3-}_4$ | 1.85 |
| $CO^{2-}_3/PO^{3-}_4$ | 0.08–0.25 |

Figure 6:
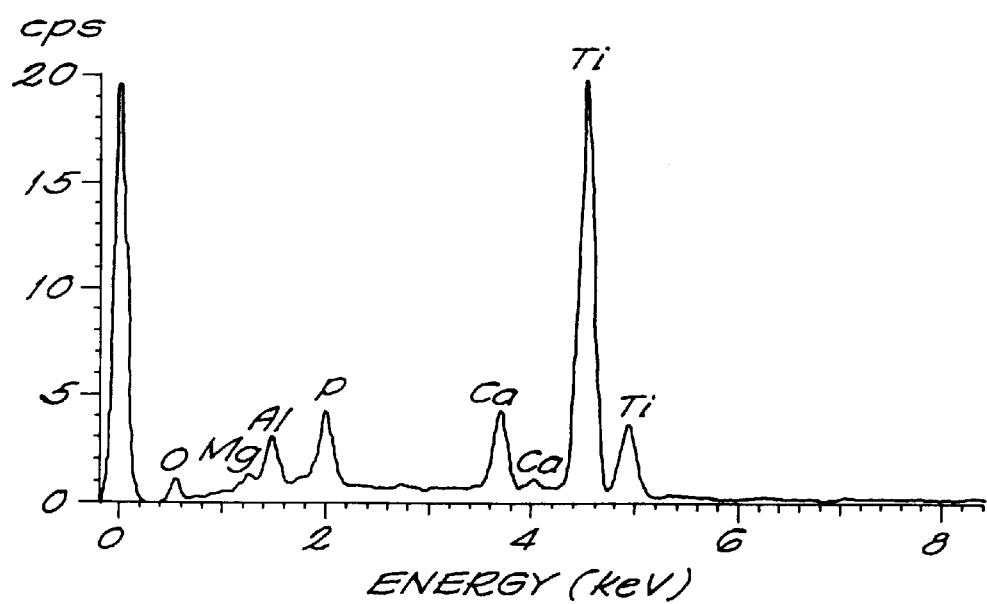
FIG. 6 is a trace obtained by Energy Dispersive X-Ray (EDX) analysis of the coating shown in FIGS. 1–3.

FIG. 6 is an EDX trace of the coating shown in FIGS. 1–3. This trace confirms the presence of calcium phosphate and magnesium in the ceramic coating.

Chemical bonding of the coating to the substrate ensures excellent adhesion of the coating to the substrate. The coating may be applied at virtually any thickness as determined by process parameters explained below. The thickness of the coating is generally in the range of about 0.005–50 micrometers, more preferably about 0.2 to 5 micrometers.

The coating of the present invention can be applied to a variety of substrates including silicon, metals, ceramics, and polymers. Exemplary metal substrates include titanium, titanium alloys, cobalt-chromium alloys, tantalum, tantalum alloys, and stainless steel. Polymeric substrates include ultra high molecular weight polyethylene, polyethylene oxide, polylactic acid, polyglycol acid and copolymers of polylactic acid and polyglycol acid.

The substrates to which the coatings are applied can be used in a variety of applications. However, the substrates are particularly well-suited for use with bioimplantable substrates, such as bone prostheses and dental implants. Exemplary bone prostheses include components of artificial joints such as knee, hips, shoulders, and elbows.

The coating of the present invention offers numerous benefits. Because of its chemical similarity to natural bone, the coating possesses high biocompatibility and it is able to encourage rapid bone ingrowth. The coating is also able to be applied in thin, uniform layers. As a result, it can be applied to complex surface geometries such as porous undercut and recessed surfaces. Despite application to such regions, the coating does not alter the surface geometry of the substrate.

The present invention also provides an efficient and effective process for applying a ceramic bone mineral-like coating to a substrate. According to this process, an aqueous solution is provided, having a pH in the range of about 5 to 10, and more preferably about 6.5 to 8.5. The coating contains at least calcium, magnesium, phosphate, and carbonate ions. Optionally, the solution may also contain ions of sodium, potassium, chlorine, sulfates, silicate, and mixtures thereof. The coating process of the invention is conducted at a relatively low temperature, preferably less than 100° C. and most preferably in the range of about 30° to 40° C. The most preferred temperature is about 34° C. to 38° C.

The substrate, or a portion of the substrate, is immersed in the solution for a period of time sufficient to enable the solution to react with the substrate to form the coating thereon. The substrate is usually immersed in the solution for about 1 to 7 days. One of ordinary skill in the art will appreciate, however, that a variety of factors, such as concentration of the major components (e.g., calcium, phosphate, magnesium, and hydrocarbonate), pH, and the environment in contact with the solution, will affect the process duration. Generally, the coating thickness increases with immersion time. It is believed that the substrate surface is converted into the calcium phosphate coating material as a result of the immersion within the solution.

A suitable solution is prepared by adding to deionized water the necessary components to obtain the desired ions upon dissociation. In one embodiment, as noted above, the solution need only contain calcium ions, magnesium ions, phosphate ions, and carbonate ions in the concentration range noted below in Table 2. Optionally, sodium, potassium, chlorine, sulfate, and silicate ions may be present in the solution at the concentration range noted in Table 1. Tris(hydroxymethyl)aminomethane may be added to the solution at a concentration range from about 1 to 100 mM to control pH. In addition, hydrogen peroxide may be added at 1–50 mM to facilitate chemical bonding between the substrate and the coating. Tables 2 and 3 illustrate exemplary constituents of the solution and exemplary compounds that can be added to the solution to obtain the desired ions.

TABLE 2

Exemplary Constituents

| Ion | mM |
| --- | --- |
| Na+ | 130–200 |
| K+ | 3.5–7 |
| $Mg^{2+}$ | 0.7–2 |
| $Ca^{2+}$ | 2–4 |
| $Cl^-$ | 96–250 |
| $HCO_3^-$ | 5–50 |
| $SO_4^{2-}$ | 0–1 |
| $HPO_4^{2-}$ | 1–2.5 |

TABLE 3

Exemplary Solution-forming Compounds

NaCl
KCl
$K_2HPO_4 \cdot 3(H_2O)$
$MgCl_2 \cdot 6(H_2O)$
HCl
$CaCl_2$
$Na_2SO_4$
$NaHCO_3$ In one embodiment the solution is exposed to a controlled environment which includes an artificial atmosphere containing about 0.001 to 10 mole percent carbon dioxide, and more preferably less than about 3 mole percent carbon dioxide. The balance of the atmosphere may include oxygen, nitrogen, argon, hydrogen, water steam, ammonia, and mixtures thereof. The artificial atmosphere can be passed over the solution at a flow rate ranging from 0 to about 10 liters per minute for every liter of solution.

The interaction among the artificial atmosphere, the solution, and the substrate leads to the conversion of the implant surface to a bone mineral-like ceramic. This coating is formed on all surfaces of the substrate that are exposed to the solution, including those that are recessed, undercut, flat, concave, convex or of any other desired shape or orientation. Further, the solution is able to penetrate small pores and voids in the surface in the material so as to form a coating on a substrate of virtually any surface geometry or surface texture. Thus, the coating can be formed on implants with complicated geometrical features, including beaded substrates which have a porous surface such as those designed for biological fixation. A particular advantage of the process of the invention is that the surfaces of such substrates, particularly those present on biological implants, are expected to stimulate bone ingrowth and to increase bone apposition. Thus, the process provides an effective technique to combine a bone mineral-like ceramic with a porous surface so that a quick and strong fixation can be achieved with the implants. The adhesion strength of the coating to a polished substrate is believed to be in excess of 30 MPa.

Figure 7:
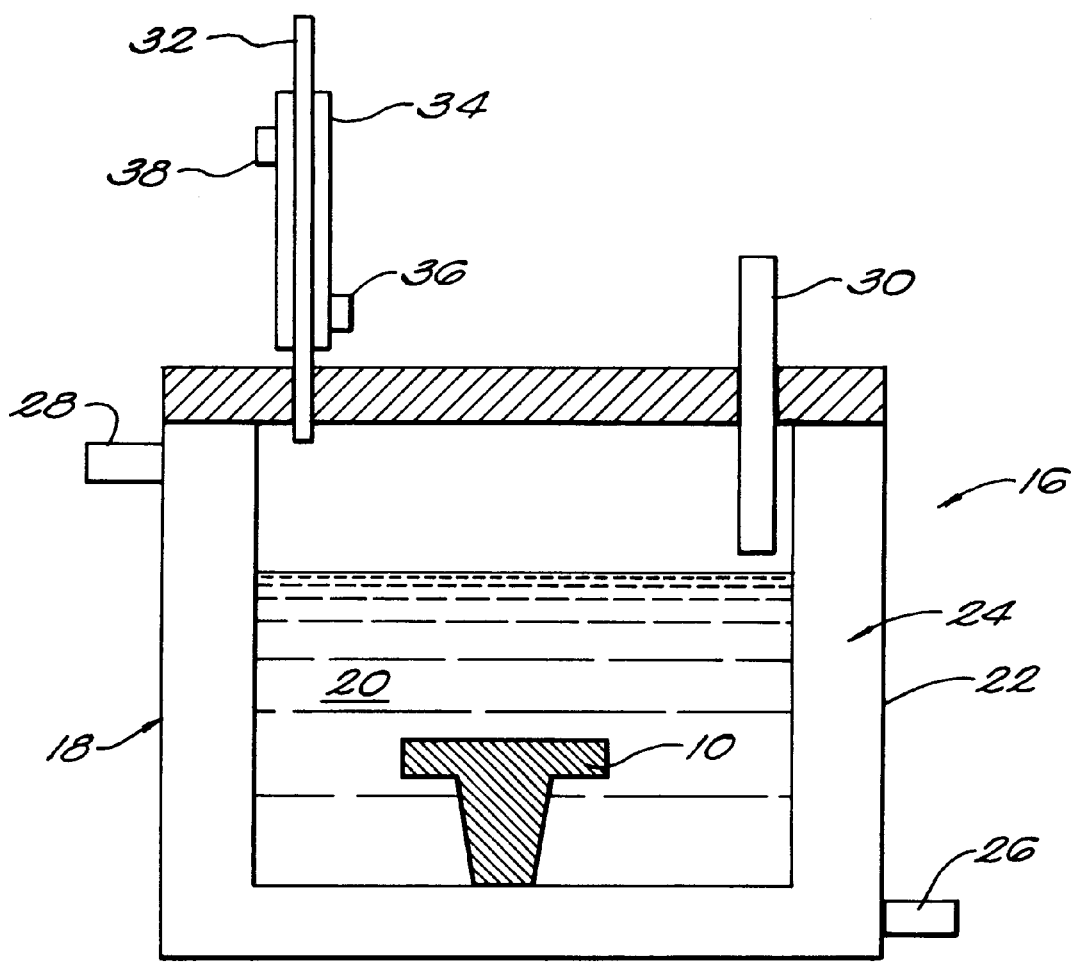
FIG. 7 is schematic view of a reactor vessel suitable to effect the process of the invention.

FIG. 7 illustrates a reactor vessel system 16 that is useful to effect the process of the invention. The reactor vessel includes a chamber 18 for containing an aqueous solution 20. Preferably, the chamber 18 is defined by a double walled structure 22 that includes an internal space 24 for accommodating a cooling fluid such as water. In one embodiment, the cooling fluid may be circulated at a temperature of about 37° C. The reactor vessel 16 includes a cooling fluid input port 26 and a cooling fluid output port 28. The reactor vessel 16 also includes a gas inlet port 30 for directing an artificial atmosphere into the reactor vessel and into contact with the aqueous solution. A gas outlet port 32 is also present to vent gas from within the vessel. In the illustrated embodiment, the gas outlet port 32 is surrounded by a cooling jacket 34 with coolant inlet and outlet ports 36, 38 to cool the exiting gas. In one embodiment cold water (e.g., at about 2° C.) is circulated through the cooling jacket.

As noted above, the composition of the aqueous solution can vary within certain limits. Table 4 provides examples of various suitable compositions of the aqueous solution.

TABLE 4

Composition of the Aqueous Solution

| (mM) | Na+ | K+ | $Mg^{2+}$ | $Ca^{2+}$ | Cl- | $HPO_4^{2-}$ | $HPO_4^{2-}$ | $SO_4^{2-}$ | tris* | pH/37° C. |
|---|---|---|---|---|---|---|---|---|---|---|
| Example I    | 178.7 | 6.24 | 1.88 | 2.81 | 202.5 | 1.74 | 27.0 | 0.63 | 50 | 7.15 |
| Example II   | 178.6 | 6.29 | 1.88 | 2.66 | 201.4 | 1.66 | 27.0 | 0.63 | 50 | 7.40 |
| Example III  | 178.7 | 6.24 | 1.88 | 2.81 | 202.5 | 1.74 | 27.0 | 0.63 | 50 | 7.15 |
| Example IV   | 178.7 | 6.24 | 1.88 | 2.81 | 202.5 | 1.74 | 27.0 | 0.63 | 50 | 7.15 |
| Example V    | 178.6 | 6.25 | 1.88 | 2.80 | 202.5 | 1.75 | 27.0 | 0.63 | 50 | 7.25 |
| Example VI   | 178.6 | 6.25 | 1.88 | 2.80 | 202.5 | 1.75 | 27.0 | 0.63 | 50 | 7.25 |
| Example VII  | 178.6 | 6.25 | 1.88 | 2.80 | 202.5 | 1.75 | 27.0 | 0.63 | 50 | 7.25 |
| Example VIII | 178.6 | 6.25 | 1.88 | 2.80 | 202.5 | 1.75 | 27.0 | 0.63 | 50 | 7.25 |

*tris(hydroxymethyl)aminomethane

Table 5 illustrates various parameters of the coating process, as well as a variety of substrates able to be coated according to the process of the present invention.

TABLE 5

Substrates and Parameters of the Process.

| | Substrate | a.a.*($CO_2$ + $O_2$) mol % $CO_2$ | Flow Rate (l.p.m.) | Temperature (° C.) solution outlet | Time (day) |
|---|---|---|---|---|---|
| Example I    | c.p. Ti disk**    | 1.0 | 5.0 | 37.0 | 4.0 | 2 |
| Example II   | CoCr disk         | 0.0 | 5.0 | 37.0 | 4.0 | 2 |
| Example III  | S-ROM sleeve      | 1.0 | 2.5 | 37.0 | 4.0 | 3 |
| Example IV   | S-ROM cup         | 1.0 | 0.0 | 37.0 | 4.0 | 3 |
| Example V    | knee femoral comp. | 1.0 | 2.0 | 37.0 | 2.0 | 2 |
| Example VI   | knee tibia comp.  | 1.0 | 0.0 | 37.0 | 2.0 | 4 |
| Example VII  | Ti6A14V disk      | 0.0 | 0.5 | 37.0 | 2.0 | 4 |
| Example VIII | Ti6A14V disk      | 1.0 | 0.5 | 37.0 | 2.0 | 4 |

*a.a. = artificial atmosphere
**c.p. = commercially pure

Although the present invention is described with respect to particular embodiments and features and uses, numerous variations or equivalents are possible without departing from the spirit or scope of the claimed invention. All references cited herein are expressly incorporated by reference in their entirety.

What is claimed is:

1. An implantable article, comprising:
   a biocompatible substrate; and
   a bioactive surface coating chemically bonded to the substrate surface over at least a portion of the substrate, the coating comprising a non-hydroxyl containing carbonated calcium phosphate bone mineral nanocrystalline apatite with chemically adsorbed water having a crystal size less than about 1 μm.

2. The article of claim 1 wherein the coating has a thickness in the range of about 0.005 to 50 μm.

3. The article of claim 1 wherein the coating has a molar ratio of carbonate groups to phosphate groups in the range of about 1:100 to 1:3.

4. The article of claim 3 wherein the coating contains ions selected from the group consisting of sodium, calcium, magnesium, sulfate, silicate, chlorine, and mixtures thereof.

5. The article of claim 4 wherein the atomic ratio of magnesium to calcium present in the coating is in the range of 1:100 to 1:4.

6. The article of claim 1 wherein the substrate is selected from the group consisting of silicon, metals, ceramics and polymers.

7. The article of claim 6 wherein the substrate is a metal selected from the group consisting of titanium, titanium alloys, cobalt-chromium alloys, tantalum, tantalum alloys, and stainless steel.

8. The article of claim 6 wherein the substrate is a polymer selected from the group consisting of ultrahigh molecular weight polyethylene, polyethylene oxide, polylactic acid, polyglycol acid, and copolymers of polylactic acid and polyglycol acid.

9. The article of claim 1 wherein the substrate is a component of a joint prosthesis.

* * * * *